United States Patent
Hauser et al.

(10) Patent No.: US 12,111,278 B2
(45) Date of Patent: Oct. 8, 2024

(54) PORTABLE IMPEDANCE BASED CHEMICAL SENSOR

(71) Applicants: The Board of Trustees of the University of Alabama, Tuscaloosa, AL (US); The U.S. Army, Edgewood Chemical and Biological Center, Aberdeen Proving Ground, MD (US)

(72) Inventors: Adam Hauser, Tuscaloosa, AL (US); Jennifer Rose Soliz, Ellicott City, MD (US); Smriti Ranjit, Tuscaloosa, AL (US)

(73) Assignees: The Board of Trustees of the University of Alabama, Tuscaloosa, AL (US); The U.S. Army, Edgewood Chemical and Biological Center, Aberdeen Proving Ground, MD (US)

( * ) Notice: Subject to any disclaimer, the term of this patent is extended or adjusted under 35 U.S.C. 154(b) by 1051 days.

(21) Appl. No.: 16/398,825

(22) Filed: Apr. 30, 2019

(65) Prior Publication Data

US 2020/0249190 A1     Aug. 6, 2020

Related U.S. Application Data

(60) Provisional application No. 62/799,660, filed on Jan. 31, 2019.

(51) Int. Cl.
| | | |
|---|---|---|
| *G01N 27/22* | (2006.01) | |
| *G01N 27/02* | (2006.01) | |
| *G01N 29/22* | (2006.01) | |

(52) U.S. Cl.
CPC ......... *G01N 27/221* (2013.01); *G01N 27/026* (2013.01); *G01N 29/226* (2013.01); *G01N 2027/222* (2013.01)

(58) Field of Classification Search
None
See application file for complete search history.

(56) References Cited

U.S. PATENT DOCUMENTS 4,851,303 A * 7/1989 Madou ............ B01J 27/12
429/491
5,141,868 A * 8/1992 Shanks ............ G01N 27/3276
422/417

(Continued)

FOREIGN PATENT DOCUMENTS

CN    108251808 A  *  7/2018  ......... C23C 14/0605

OTHER PUBLICATIONS

Holly Hedegaard, Margaret Warner, and Arialdi M Miniño, Drug Overdose Deaths in the United States, 1999-2016. (US Department of Health and Human Services, Centers for Disease Control and Prevention, National Center for Health Statistics, 2017), 8 pages.

(Continued)

*Primary Examiner* — Matthew D Krcha
(74) *Attorney, Agent, or Firm* — Meunier Carlin & Curfman LLC (57) ABSTRACT

An apparatus for sensing a target analyte includes a sensing material of a baseline composition. The sensing material is in electrical communication with an alternating energy input across the sensing material at a first frequency. The sensing material is configured to be placed within an environment such that an exposed state is in communication with a concentration of a target analyte proximate the sensing material, and wherein the target analyte changes at least one compositional property of the baseline composition. An impedance detection device is connected to a sensing circuit and receives an output from the sensing material, the output exhibiting a respective impedance value of the sensing material corresponding to the input for the first frequency.

(Continued)

The respective impedance value is dependent upon the concentration of the target analyte in the environment and the first frequency.

17 Claims, 4 Drawing Sheets

(56) References Cited

U.S. PATENT DOCUMENTS

| | | | | |
|---|---|---|---|---|
| 2014/0028327 | A1* | 1/2014 | Potyrailo | G01R 35/005 324/601 |
| 2017/0370867 | A1* | 12/2017 | Davis | H01L 31/115 |
| 2018/0080891 | A1* | 3/2018 | Potyrailo | G01N 33/0036 |

OTHER PUBLICATIONS

Matthew P Prekupec, Peter A Mansky, and Michael H Baumann, "Misuse of novel synthetic opioids: a deadly new trend" Journal of addiction medicine 11 (4), 256 (2017).

Joji Suzuki and Saria El-Haddad,"A review: fentanyl and non-pharmaceutical fentanyls" Drug and alcohol dependence 171, 107-116 (2017).

Gladden RM, Martinez P, Seth P. Fentanyl Law Enforcement Submissions and Increases in Synthetic Opioid-Involved Overdose Deaths—27 States, 2013-2014. MMWR Morb Mortal Wkly Rep 2016;65:837-843. DOI: http://dx.doi.org/10.15585/mmwr.mm6533a2external icon.

Laura M Matz and Herbert H Hill,"Evaluation of opiate separation by high-resolution electrospray ionization-ion mobility spectrometry/mass spectrometry" Analytical chemistry 73 (8), 1664-1669 (2001).

Ahmed Jehanli, Sean Brannan, Lesley Moore, and Vina R Spiehler, "Blind trials of an onsite saliva drug test for marijuana and opiates" Journal of Forensic Science 46 (5), 1214 (2001).

John F Casale, Jennifer R Mallette, and Elizabeth M Guest,"Analysis of illicit carfentanil: emergence of the death dragon" Forensic chemistry 3, 74-80 (2017).

Simona Pichini, Renata Solimini, Paolo Berretta, Roberta Pacifici, and Francesco Paolo Busardò, "Acute intoxications and fatalities from illicit fentanyl and analogues: an update" Therapeutic drug monitoring 40 (1), 38 (2018).

Harris, Coleman R., et al. "Sensing of NO 2 with zirconium hydroxide via frequency-dependent electrical impedance spectroscopy." Dalton Transactions 46.33 (2017): 10791-10797.

Jennifer R. Soliz, Andrew D. Klevitch, Coleman R. Harris, Joseph A. Rossin, Amy Ng, Rhonda M. Stroud, Adam J. Hauser, and Gregory W. Peterson, "Structural Impact on Dielectric Properties of Zirconia" The Journal of Physical Chemistry C 120 (47), 26834 (2016).

Gregory W Peterson, Monica Mcentee, Coleman R Harris, Andrew D Klevitch, Augustus W Fountain, JR Soliz, A Balboa, and AJ Hauser, "Detection of an explosive simulant via electrical impedance spectroscopy utilizing the UiO-66-NH 2 metal-organic framework" Dalton Transactions 45 (43), 17113 (2016).

Samir D Roy and Gordon L Flynn,"Solubility and related physicochemical properties of narcotic analgesics" Pharmaceutical research 5 (9), 580 (1988).

Robert S Bowman, Grace M Haggerty, Roger G Huddleston, Daphne Neel, and Matthew M Flynn, (ACS Publications, 1995). Bowman, Robert S., et al. "Sorption of nonpolar organic compounds, inorganic cations, and inorganic oxyanions by surfactant-modified zeolites." 1995. 54-64.

Patryk Oleszczuk, Bo Pan, and Baoshan Xing,"Adsorption and desorption of oxytetracycline and carbamazepine by multiwalled carbon nanotubes" Environmental science & technology 43 (24), 9167 (2009).

Roland JM Pellenq, Bernard Tavitian, Didier Espinat, and Alain H Fuchs, "Grand canonical Monte Carlo simulations of adsorption of polar and nonpolar molecules in NaY zeolite" Langmuir 12 (20), 4768-4783 (1996).

\* cited by examiner

FIG. 1

Fig 2. Current change in Zr(OH)$_4$ exposed to NO$_2$ and 80% relative humidity[4].

Fig 3. DMMP and DMCP response in (a) impedance magnitude |Z| and (b) resistivity R for Fe$_2$O$_3$ nanoparticles.

Fig 4. Impedance magnitude |Z| of Ag-doped graphene oxide (Ag-GO) films in vacuum, 50% relative humidity, agent simulant (DMCP) and interferents. Box shows frequency window for selective DMCP sensing.

FIG. 5

PORTABLE IMPEDANCE BASED CHEMICAL SENSOR

CROSS REFERENCE TO RELATED APPLICATIONS

This application claims the benefit of priority and incorporates entirely by reference U.S. Provisional Patent Application Ser. No. 62/799,660 filed on Jan. 31, 2019.

STATEMENT REGARDING FEDERALLY SPONSORED RESEARCH

This invention was made with government support under grant No. W911NF-16-2-0073 awarded by the Department of Defense, United States Army Research Office. The Government has certain rights in the invention.

FIELD

A sensor according to this disclosure may be used to identify unique frequency modulations relative to an input AC signal across a sensor material and use the frequency modulations to detect the presence of certain chemicals in a given environment.

BACKGROUND

Current technologies for chemical sensors are often too large to be easily portable (e.g., greater than 40 lbs.), too expensive for extensive implementation (e.g. greater than $100k), or are insufficient due to non-selective measurement methodologies (e.g., DC resistivity applications). Standard-bearers for sensors directed to identifying chemical agents that can be used as weapons of mass destruction, opiate manufacturing, and other harmful scenarios include:
 (i) Mass Spectrometry;
 (ii) Gas Chromatography;
 (iii) Ion Mass Spectrometry;
 (iv) Airport "Puffer Machines" (one of the smaller sensors in use); and
 (v) Electric Noses ("e-Noses") that currently use DC (Direct Current) to probe for electrical changes due to chemical vapors.

Even though some of these prior art equipment types are becoming more compact than standard applications of the past, most are still too large for portable operations or for installation in areas that require discreet, mobile use in dangerous circumstances. Furthermore, these kinds of chemical sensors have the drawback that chemical detection is limited, and the devices provide only a single scalar output. Accordingly, these kinds of prior art sensors present little in the way of sensitivity and selectivity when more than one target analyte needs to be detected by a single unit having only one sensor material.

One example of deficiencies in prior art chemical detectors is illustrated in the illegal drug trafficking arena. The National Survey of Drug Use and Health found over two million Americans have an opioid use disorder, over eleven million have misused prescription opioids, and hundreds of new users emerge every day [1,4]. First responders and law enforcement are endangered since accidental inhalation or absorption can be lethal. Without rapid detection, overdose responses are also slowed, with lethal consequences. The economic cost of the opioid crisis now exceeds half a trillion dollars annually, in addition to enriching criminals.[1] Synthetic opioids are also a major concern for national security and defense as they can be weaponized. No portable test system exists, and domestic opioid inventory has skyrocketed: Simple traffic stops have found enough fentanyl behind a single truck panel, 118 lbs., to kill 26 million people if aerosolized. While the danger of chemical attack is clear, solutions are lacking: port-of-entry detection using larger equipment[5] does not address the quantities obtainable from domestic producers, including drug companies. The leading rapid response technique for portable fentanyl and fentanyl analog detection uses lateral flow chromatographic immunoassay (LFCA) to detect these analogs down to 10-20 ng/mL in urine and saliva. LFCA relies on external liquid input, color-change interpretation, and a 5-minute wait time.[6] While it may help first responders and opioid users identify danger, it does not protect from accidental exposure or chemical attack. Further, chemists employed in illicit opioid markets continuously create new analogs missed by LFCA and non-portable techniques such as Ion Mobility Spectroscopy (IMS) and Gas Chromatography (GC). [7,8] While Gas Chromatography can be recalibrated for new analogs, even semi-portable non-contact systems do not exist.[5]

Finally, companies are developing portable non-contact sensors. Smiths
Detection's portable spectroscopic test is "non-contact" but has low sensitivity, must be actively pressed against material, and is prone to accidental contact. Vaporsens' direct current "e-nose" system will suffer from the same selectivity issues as similar systems already available and the technology requires transport away from the scene to be attached to a larger analysis system.

Given numerous drawbacks and limitations of prior art devices, a need exists in the art of chemical sensing for a portable device that can selectively identify a variety of target analytes in multiple kinds of environments. In particular, the field needs a chemical detection apparatus that can use a single sensor material and provide concentration information for the target analyte by analyzing an electrical response exhibited by the sensor material in various environmental conditions.

SUMMARY

An apparatus for sensing a target analyte includes a sensing material comprising a baseline composition, wherein the sensing material is in electrical communication with an energy source that directs an input of either an AC voltage or an AC current across the sensing material at a first frequency, at least a portion of the sensing material positioned in an exposed state relative to an environment. The sensing material is configured to be placed within the environment such that the exposed state comprises a concentration of a target analyte proximate the sensing material, and wherein the target analyte changes at least one compositional property of the baseline composition. An impedance detection device is connected to a sensing circuit and receiving an output from the sensing material, the output exhibiting a respective impedance value of the sensing material corresponding to the input for the first frequency. The respective impedance value is dependent upon the concentration of the target analyte in the environment and the first frequency.

BRIEF DESCRIPTION OF THE DRAWINGS

The accompanying drawings, which are in and constitute a part of this specification, illustrate certain examples of the present disclosure and together with the description, serve to explain, without limitation, the principles of the disclosure. Like numbers represent the same element(s) throughout the figures.

DETAILED DESCRIPTION

The following description of the disclosure is provided as an enabling teaching of the disclosure in its best, currently known embodiment(s). To this end, those skilled in the relevant art will recognize and appreciate that many changes can be made to the various embodiments of the embodiments described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this disclosure belongs.

A sensor and a sensing element may be used interchangeably to denote a structure made of a sensing material with a purpose of effecting the physical changes described below in the presence of a target analyte.

As used in the specification and claims, the singular form "a," "an," and "the" include plural references unless the context clearly dictates otherwise. For example, the term "an agent" includes a plurality of agents, including mixtures thereof.

As used herein, the terms "can," "may," "optionally," "can optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Publications cited herein are hereby specifically by reference in their entireties and at least for the material for which they are cited.

Figure 1:
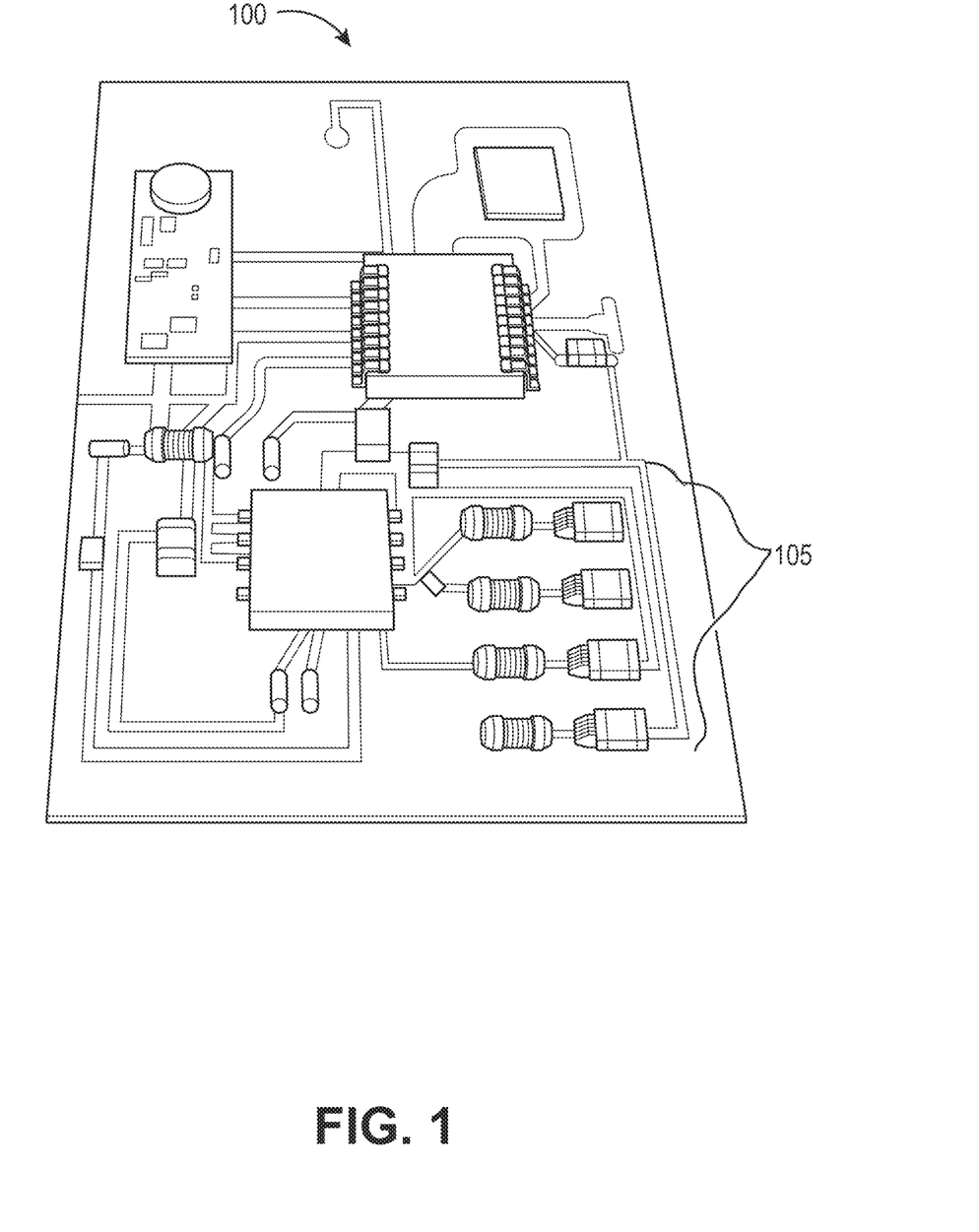
FIG. 1 is a schematic representation of an impedance detection circuit for use in conjunction with a portable sensor as set forth herein.
Figure 2:
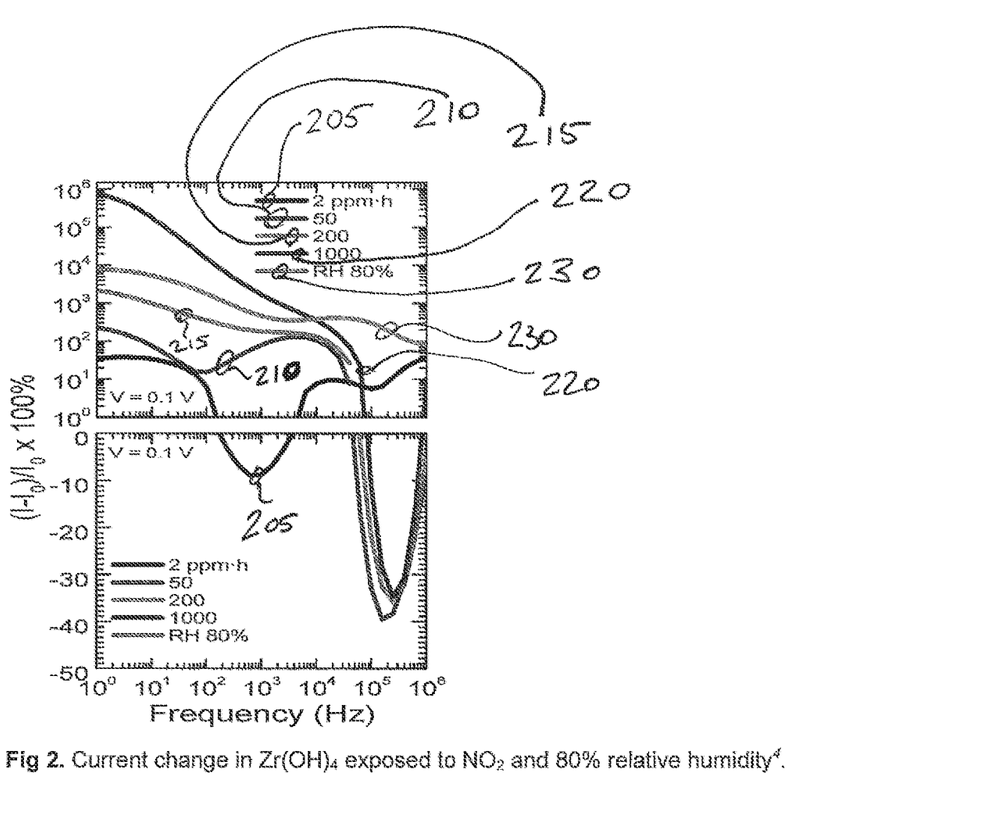
FIG. 2 is a schematic representation of a current change in $Zr(OH)_4$ exposed to $NO_2$ and 80% relative humidity.[4]

In one general sense, the devices, systems, and methods disclosed herein exploit frequency-dependent impedance spectroscopy (FDIS) to develop portable, non-contact detection devices for various target analytes, including but not limited to the above described fentanyl and fentanyl analogs. By using materials physics, selective chemistry, and appropriate analyzer circuits, new functional devices are described herein that can provide chemical sensing capabilities at the interface of basic science and applied engineering. The materials, electrical circuits, and processing capabilities described herein may be used to build a new class of sensors that provide alternating current (AC) probes of adsorbent materials to "sniff out" select target analytes (such as, but not limited to, fentanyl analogs) in a safe, non-contact manner. While current "electronic noses" use direct current measurements prone to low-frequency environmental interference, the AC approach allows tuning to analyte-specific dielectric changes in the sensor material, decreasing interference and improving sensitivity as shown in FIG. 2 and discussed below.

In one non-limiting example, the resultant device has a reaction time of one second or less and is transferable to all airborne chemical detection scenarios requiring a flexible device with a small footprint (e.g., one square inch or less). The work will enable new sensors and research in defense, medicine, life sciences, and industrial chemistry. This disclosure makes use of at least the following points: (1) application of AC sensing to drive sensitivity, (2) use of nonpolar, hydrophobic, sensor materials to mitigate masking effects and drive relative sensitivity, and (3) application of FDIS and algorithms to achieve full selectivity and differentiation of a target analyte and analogs thereof. Other related research may also use the circuits and sensors described herein for colorimetric analysis across a given spectrum and analyze a chemical detection response according to light emissions from a sensor in a given environment.

In one embodiment of this disclosure, an apparatus uses frequency modulation of a known AC input to determine if compositional changes to a sensor material in the presence of a target analyte cause a sufficient change in an electrical response of the sensor material. By directing an alternating signal through, within, or across the sensor material, an analyzer circuit can use an output electrical signal from the sensor material to determine whether a target analyte has affected the sensor material in a way that led to a pre-defined frequency modulation response. Various frequency modulation responses for a single sensing material can be indicative of not only the presence of a target analyte but also respective concentrations of the target analyte. One non-limiting theory of operation for certain embodiments described below is that electron "freedom" changes when airborne chemicals (or even liquid and solid states of a target analyte) land on, interact with, connect to and/or bond or adsorb with a sensor material. In this regard, many embodiments described below utilize shifts in the intrinsic dielectric properties of a sensing material when the sensing material is in a presence of a target analyte to monitor frequency modulation profiles for an electrical signal traversing the sensor material. By looking at an overall electrical response of a sensing material in the presence of different target analytes, the same sensing material in a single sensor can be used to identify a target analyte by a type, a binary presence or absence, a concentration at discrete points in time, and a concentration response over a time period. In one non-limiting example, the electrical response used to identify a target analyte proximate a sensor is an AC impedance response across a frequency spectrum. An output detection circuit can alert a user when one of many AC impedance profiles for a sensing material has been triggered by the presence of a target analyte at a given concentration. In this regard, one sensing node may now be considered as an equivalent to many sensing nodes in that documented impedance profiles from test cases can direct the user to corresponding data suggesting the presence of respective target analytes at numerous concentrations.

This disclosure is not limited in any way by referencing the above noted shifts in a dielectric constant as one mechanism by which an electrical response of a sensor material may aid in sensor operations. Testing of various sensing materials, having numerous kinds of compositions, structural features, doping, and even dimensions, can be used to establish electrical profiles of the sensing materials in the presence of many target analytes. This disclosure explores an electrical response in the form of impedance profiles for a sensor material when subject to an AC input signal across a frequency spectrum. The presence of a target analyte may be modeled, in one respect, as causing a shift in the dielectric constant, but one of skill in the art will recognize that the dielectric constant is frequency dependent and also dependent on the initial dielectric constant value of the device, which is dependent on the material type, sensing element dimensions, etc. In addition, the frequency shift spectra may shift as one changes sensor layer thickness and other structural features.

In certain embodiments, presence of a target analyte may cause a baseline impedance to either increase or decrease for a given sensor material. Furthermore, the impedance is a complex value so the word "impedance" as used in this disclosure is fully encompassing of all components of a given impedance reading, including mean impedance magnitude, phase angle, or real an imaginary components of complex impedance. Examples herein illustrating impedance magnitude as indicative of target analyte concentration are not limiting of the disclosure but predict corresponding usefulness of phase angle changes and phase shifting features for certain sensor materials. Sensor materials may also take advantage of materials engineering, such as using dopants to help define a baseline electrical response in a sensor. Similarly, dopants and other structural features can be used to tune a sensing material for detecting a target analyte with a pre-planned electrical response in light of input AC signals having regulated frequencies. In one non-limiting embodiment, the sensing element includes a self-indicating colorimetric material that changes dielectric and/or impedance values of the sensing element upon exposure to a target analyte.

EXAMPLES

Figure 3:
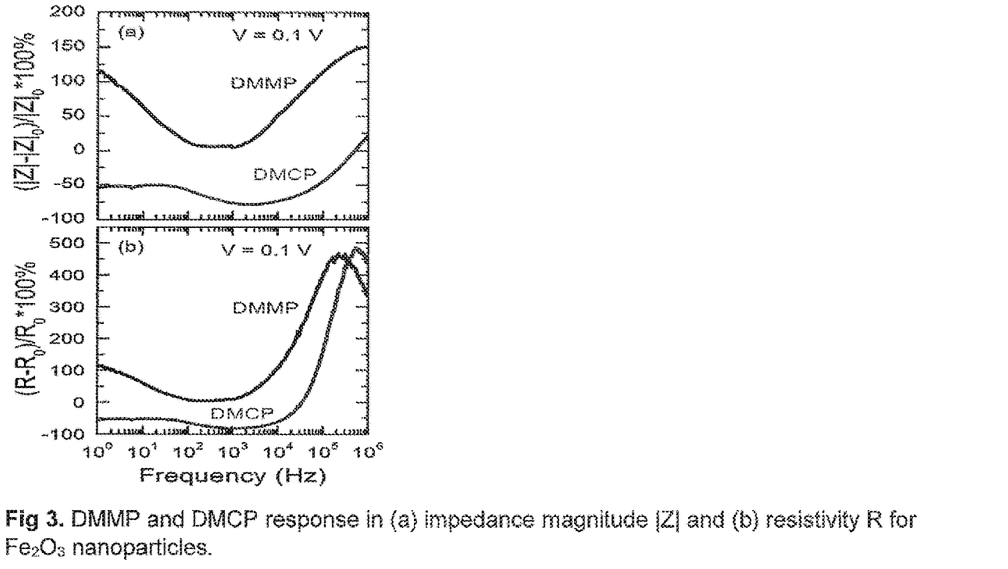
FIG. 3 is a schematic representation of the DMMP and DMCP response in (a) impedance magnitude [Z] and (b) resistivity R for Fe2O3 nanoparticles.

This disclosure includes studies regarding the capabilities of frequency-dependent impedance spectroscopy (FDIS) for airborne detection of explosives, chemical weapons, and industrial toxins in collaboration with the US Army Edgewood Chemical Biological Center (ECBC)[9-11]. Without limiting the disclosure to any single embodiment, the examples discussed below have demonstrated differentiation within single chemical agent classes (FIG. 3). In one example, since fentanyl is non-polar, the text results avoid some environmental interference by utilizing nonpolar or hydrophobic sensor materials.

However, sensor materials that are sensitive to an analyte may not be selective against water, reactive cleaners, and similar analyte chemistries. FIG. 2 is an example: $NO_2$ dosage with probe frequency <100 Hz (including direct current) results in large device current increases but is indistinguishable from water (RH 80%) under low frequency probes.

FDIS is a perfect complement to selective chemistry efforts: Probe frequencies are chosen where environmental interference, such as water vapor below 100 Hz, do not play a role. In FIG. 2, the current decreases at 900 Hz and 200 kHz inform selectivity for $NO_2$. By eliminating interferent concerns via the frequency degree of freedom, this disclosure shows an increased selectivity per sensing element, eliminates source uncertainty, and allows peak device sensitivity[12-14]. Additionally, the combination of broad-class reactivity and frequency differentiation provides flexibility to adapt to new analogs created by illicit markets and aggressors. FIG. 2 illustrates outputs for target analytes present at 2 ppm·h (205); 50 ppm·h (210); 200 ppm·h (215); 1000 ppm·h (220); and relative humidity at 80 percent (230).

The tests and examples of this disclosure include results of evaluated metal-organic frameworks, nanoparticles, metal oxides, polymers, and colorimetric materials for low vapor pressure uptake and dielectric sensitivity. Evidence indicates that metal oxides/hydroxides and colorimetric materials are the best candidates for nonpolar materials that interact with fentanyl. Certain results indicate that, with specific ligand modifications and transition metal doping of the metal oxide complex, the materials used for sensors can be engineered for strong reaction and sorption uptake of a target analyte (e.g., fentanyl) without an accompanying strong reaction to water or other common interferents. Tests have determined that dopant choice drives selectivity to given analytes via bond angle adjustments and dielectric modification of band levels to favor reactance through sorption or a specific chemical reaction. Dopant levels control sensitivity by adjusting the number of sorption/reaction sites and thus initial impedance of the material. Placing material in a state close to rapid changes in dielectric behavior creates large responses to small analyte quantities.

Figure 4:
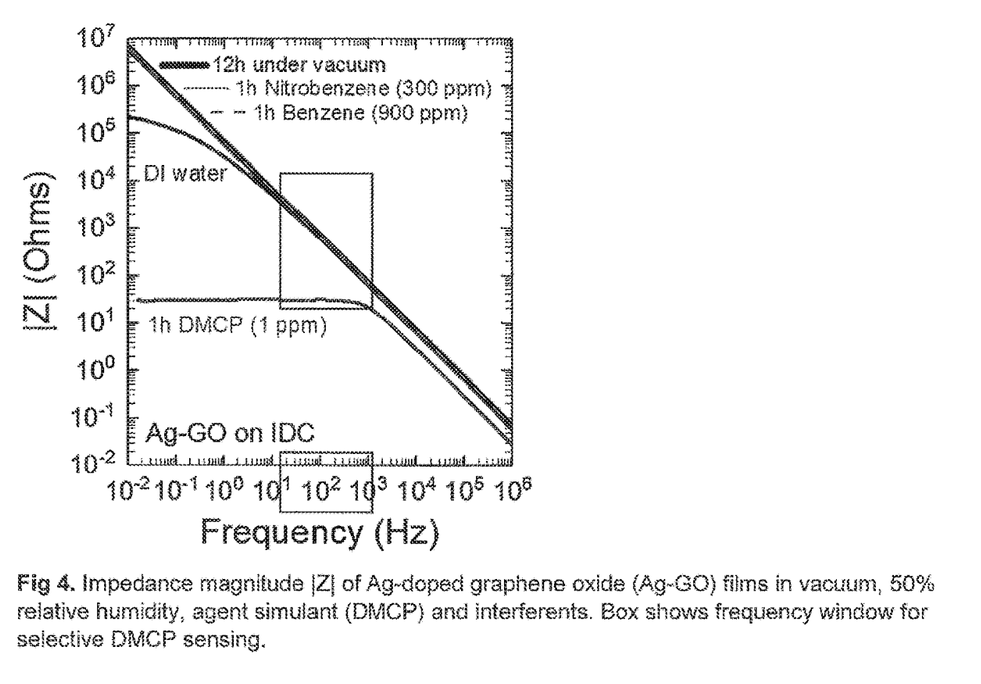
FIG. 4 is a schematic representation of an impedance magnitude [Z] of Ag-doped graphene oxide (Ag-GO) films in vacuum, 50% relative humidity, agent simulant (DMCP) and interferents and illustrating an inset box showing a frequency window for selective DMCP sensing.

FIGS. 2-3 show that even in simple unmodified metal oxides and hydroxides, the sensor disclosed herein can create selective sensing using FDIS. The claims attached to this disclosure illustrate identified hydroxide materials that react sensitively to both fentanyl and fentanyl analogs and show strong selectivity even before FDIS. Note that FIG. 3 demonstrates that, even in an undoped metal oxide, selectivity exists between two organophosphates with only one differing ligand. Given the effect of FDIS in simple oxides, the devices discussed herein will be uniquely positioned to overcome challenges such as, but not limited to those posed by the exceptionally low vapor pressure of fentanyl emitting from the inert solid. FIG. 4 shows doping for selective behavior: Undoped graphene oxide does not react to DMCP or any organophosphate.

In addition to the test results shown herein, certain deliverables are (1) non-contact, sub-minute, quantitative detection of target analytes on breath and inert material and (2)

seconds-scale "dry" detection of aerosolized analogs for immediate chemical attack detection and response.

The claims attached here identify materials with selective analyte uptake (for example, and without limitation, fentanyl uptake) and test their detection limits by applying FDIS to films on interdigitated capacitors. Uptake analysis and impedance spectroscopy testing continues to identify interferents, refine selection criteria, calibrate impedance changes with analyte concentration, and create composites. By way of example, for fentanyl analogs, colorimetric materials[13, 15] present one area of focus for this research. The wholesale shift in dielectric properties can be sensed electrically long before visual changes when water is not a complicating factor. Research has successfully demonstrated this approach using colorimetric materials designed at ECBC to target polar and nonpolar reactive analytes of interest to the military, at trace (ppb) concentrations. A series of materials have been shown to be highly selective at frequencies ranging from 100 Hz to 1 MHz. Preliminary data suggest several colorimetric materials in the ECBC catalog in which bulk powder reacts to sub-ppb airborne concentrations of fentanyl simulant. In addition to the extensive library of sensing materials already developed and made on-demand in laboratory settings, sensor materials exist in contact-required visual or spectroscopic commercial tests, so bottlenecks in design and development are unlikely.

The synthesis and sensing characterization of new sensor materials will be the majority effort of future developments in this work. The candidate metal hydroxides that will be characterized and employed appear to undergo irreversible reactions. As the vapor pressure of fentanyl and analogs is typically a few parts per trillion, sensors using these materials will be reusable with adaptive circuitry. However, materials with reversible impedance shifts will be targeted in years 2-4 to allow long-life sensors.

As criteria for selective sensing are identified, promising sensor materials will be integrated into devices that specifically target previously determined selective frequencies. These will be single-sensor-element devices, fabricated in-group to minimize iteration time, on conventional and flexible circuit boards ~2 inches wide, with on-board battery and Bluetooth transmission to a smartphone. A smartphone app and conventional software to analyze the data, show and transmit raw data, and produce reports will be designed to allow troubleshooting and data analysis. Further operations with local first responders to field-test prototype sensors and determine unexpected field interferents, design flaws, or end-user requests are available to refine the selectivity of the devices.

A parallel track for research is evaluation of test strips for FDIS adaption and improvement of sensitivity by two or more orders of magnitude. Test strip markers, typically metallic nanoparticles, are extremely sensitive to dielectric probes and FDIS is both rapid and quantitative. This disclosure indicates that tests will apply FDIS to current fentanyl test strips (limit 130 ng/mL) to evaluate impedance behaviors. A secondary deliverable is an electronic test strip reader with sensitivity <10 ng/mL. This will lower detection time. In due course, strips with improved FDIS response will be used in a prototype handheld device.

This disclosure further incorporates the concept of single-element, single-frequency devices that will be upgraded to have multiple elements and on-the-fly frequency probe reconfiguration.

Devices will gain capability to identify and distinguish multiple potential target analytes, such as fentanyl analogs. Miniaturization of impedance elements to 100-200 nm gap widths will maintain device size. Reconfiguration and multi-element sensing will require significant focus on algorithm design. Smartphone app and conventional software development will provide simplified "end-result-only" user interface data with an eye toward commercialization and Internet-of-Things (IoT) connectivity capabilities to build a large-area "web" for law enforcement, first responder, and military use.

In some embodiments, multiple sensing material elements of same or differing material types are used simultaneously or in series in a single device, each with redundant or different predetermined threshold values and the corresponding frequency values. This may be an array of sensing material elements of same or differing material types that are used simultaneously or in series, each with redundant or different predetermined threshold values and the corresponding frequency values. Indicator lights or displays give response to individual sensing element changes, or when combinations of criteria from multiple sensing elements are met. The color or behavior of the light corresponds directly to the sensing element triggered or the results of the target analyte exposure.

Figure 5:
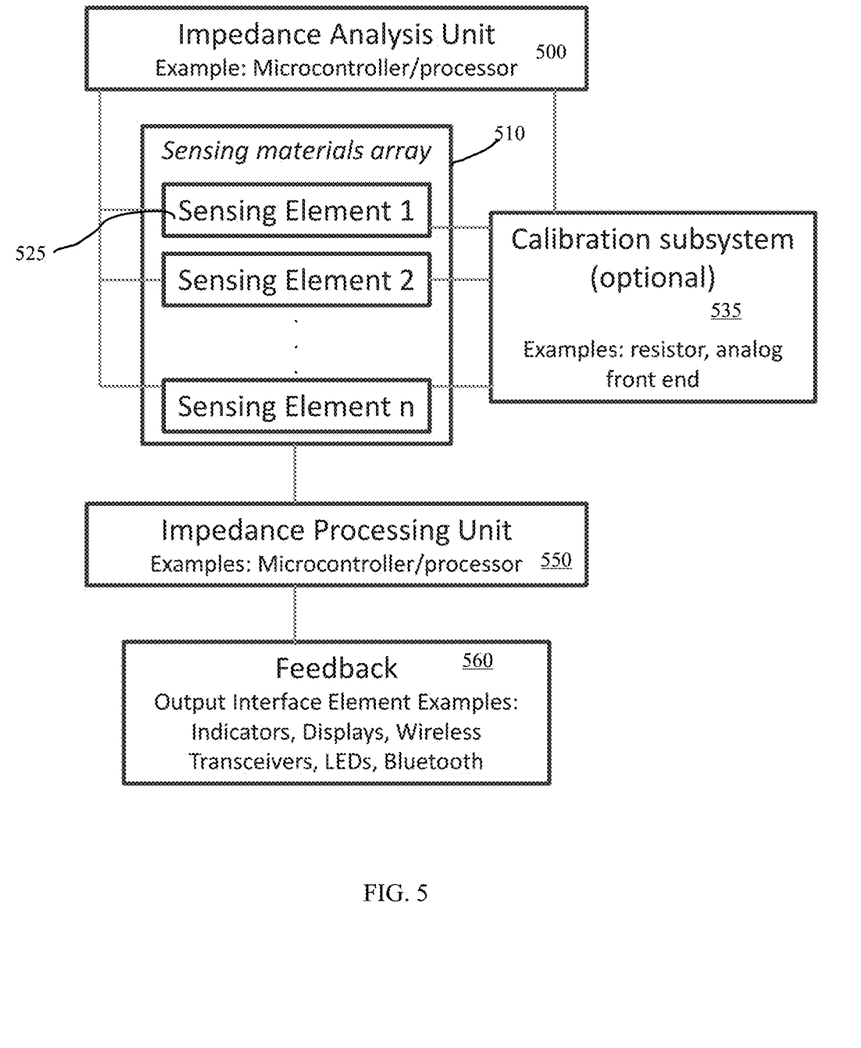
FIG. 5 is a block diagram representing embodiments of hardware configured to implement steps of a method according to this disclosure.

FIG. 5 illustrates an example of the array embodiment described above. In the operational block diagram of FIG. 5, which is shown only for example and is not limiting of this disclosure, the impedance analysis unit (500) incorporates the sensing array (510) having multiple sensing elements therein, and a calibration system (535) that is an optional accessory. A microprocessor and/or associated computer provide an impedance processing unit (550) with an output that provides appropriate feedback (560) to connected devices for alarms, displays, and the like. This embodiment is possibly configured with associated GPS systems for location services that can be monitored remotely across a network. In addition to the array mentioned in FIG. 5, a single device may include sensors operating in parallel to sense the same target analyte (e.g., a back up sensor), or additional sensors may be tuned to detect different target analytes on the same device in the same location.

In parallel, this disclosure includes embodiments that upgrade the handheld FDIS reader to a non-contact airborne detection device based on post-exposure lateral flow. Sub-minute detection in breath or inert material will use flow of rapid-evaporation liquid from an on-board reservoir, allowing non-contact field-testing from external liquid. Time-to-result will be reduced and increased sensitivity will meet the challenge of the low vapor pressure of fentanyl and its analogues.

A scale-up to multi-element and reconfigurable frequency capabilities and accompanied by a scale-down in size to a square inch or less is within the scope of this disclosure via multi-layer circuit writing and circuit optimization. Significant algorithm design for multi-element sensors will be required, but single-element algorithms already developed will shorten development time. The disclosed FDIS technique is applicable to aqueous environments. In sensing materials where water does not affect dielectric properties, constraint of the probing electric field to within the sensor layer via control of layer thickness and electrode gap width may allow an adapted circuit to be used in water treatment facilities, environmental studies, and blood testing with reduced cost and size, and add to the IoT-connected airborne sensing "web" as discussed above.

Thus, designing reliable, cheap, portable sensing and diagnostic devices across the chemical spectrum is a high priority. It is also a challenge: Chemically selective materials are rarely sensitive, and sensitive materials are rarely highly selective. The application of AC Impedance Spectroscopy will enable portable non-contact fentanyl detection, an enormous improvement upon current field techniques and one that will protect millions from harm where deployment is currently unfeasible. My group integrates electrical engineering and materials physics and has validated FDIS for trace airborne detection of explosive, toxic, and organophosphate analytes.

Combining sensitive materials with a new selective dimensionality of AC frequency is a new approach that unlocks detection thresholds by improving selectivity in materials that are sensitive but not fully selective. In some embodiments, the devices are fabricated on flexible, wearable, or transparent substrates. The substrates themselves may also be flexible, transparent, or translucent. The methodology is unique and applicable across both airborne and aqueous chemical sensing. These devices will permit, for the first time, on-site, rapid, selective, and non-contact detection via unique methodology. The project also disrupts feedback-controlled chemical processing, where tighter controls mean higher precision chemistry in the laboratory and the factory.

In accordance with the disclosure noted above, the embodiments described herein include an apparatus for sensing a target analyte, the apparatus includes a sensing material having a baseline composition, and the sensing material is in electrical communication with an energy source that directs an input of either an AC voltage or an AC current across the sensing material at a first frequency. At least a portion of the sensing material is positioned in an exposed state relative to an environment. The sensing material is configured to be placed within the environment such that the exposed state includes a concentration of a target analyte proximate the sensing material, and the target analyte changes at least one compositional property of the baseline composition. An impedance detection device connected to a sensing circuit receives an output from the sensing material, the output exhibiting a respective impedance value of the sensing material corresponding to the input for the first frequency. The respective impedance value is dependent upon the concentration of the target analyte in the environment and the first frequency. The changes in the at least one compositional property of the baseline composition are exhibited in the respective impedance value. In certain non-limiting embodiments, the baseline composition includes either a nonporous structure or a porous structure subject to binding with the target analyte to change the at least one compositional property of the baseline composition. The structure may include at least one of a metal oxide, a metal hydroxide, a mixed-metal oxide and a mixed metal hydroxide. The mixed-metal oxide or said mixed metal hydroxide may be one or more or combinations of zirconium oxide/hydroxide, titanium oxide, barium titanium oxide, barium titanium zirconium oxide, barium zirconium oxide, zirconium-titanium oxide/hydroxide, silicon-aluminum hydroxide; iron-silicon-aluminum hydroxide; silicon-aluminum-titanium hydroxide, and silicon-aluminum-titanium-phosphorus hydroxide. The metal oxide/hydroxide or mixed-metal oxide/hydroxide may be one or more or combinations of zirconium oxide/hydroxide, titanium oxide, barium titanium oxide, barium titanium zirconium oxide, barium zirconium oxide, zirconium-titanium oxide/hydroxide, silicon-aluminum oxide/hydroxide; silicon-aluminum-titanium oxide/hydroxide, silicon-aluminum-titanium-phosphorus oxide/hydroxide; zirconium oxide/hydroxide; vanadium oxide/hydroxide; iron oxide/hydroxide; manganese oxide/hydroxide; cobalt oxide/hydroxide; copper oxide/hydroxide; nickel oxide/hydroxide; niobium oxide/hydroxide; tantalum oxide/hydroxide; molybdenum oxide/hydroxide; tungsten oxide/hydroxide; chromium oxide/hydroxide; or mixtures thereof. The baseline composition may also be a porous metal oxide/hydroxide or porous mixed-metal oxide/hydroxide, such that target analytes directly react inside the pore structure of said porous metal oxide/hydroxide or porous mixed-metal oxide/hydroxide.

In other embodiments, the baseline composition includes a reactant configured to exhibit a chemical reaction with the target analyte. The baseline composition includes a transition metal or cation reactant suitable to react with the target analyte or a byproduct thereof. In other embodiments, the transition metal reactant may include salts, acetates, nitrates, sulfides, chlorides, oxides, or oxyhydroxides of chromium, cobalt, copper, iron, manganese, nickel, or lanthanides. Accordingly, the transition metal reactant may be one or more or combinations of $CoCl_2$, $CoS_2$, $Co(NO_3)_2$, $Co(NH_3)_2$, $Co(acetate)_2$, $CuS_2$, $CuCl_2$, $Cu(NO_3)_2$, $Cu(NH_3)_2$, $Cu(acetate)_2$, $Ni(NO_3)_2$, $Ni(NH_3)_2$, $NiS_2$, $NiCl_2$, $FeCl_3$, $FeS_3$, $Fe(NO_3)_3$, $Fe(NH_3)_3$, $Ln(NO_3)_x$ (Ln=lanthanides), or $Ln(acetate)x$. A toxic chemical directly reacts with a surface of said transition metal or cation reactant. In certain embodiments of this disclosure, the transition metal or cation reactant is present at a concentration of 1 to 90 weight percent.

This disclosure further embodies baseline compositions that utilize a film, and optionally, the film may be attached to a substrate. The output of sensors described herein include either an AC voltage output or an AC current output. The input to the sensor maintains the same magnitude across respectively different frequencies in a frequency spectrum. In certain implementations, an energy source scans a series of AC voltage inputs or AC current inputs at respective frequencies in a frequency spectrum across the sensing material. The baseline composition of the sensor material may utilize a baseline impedance profile, wherein a change in respective impedance values relative to the baseline impedance profile of the sensing material across the frequency spectrum is greater than a threshold impedance change value and indicates presence of the target analyte at the sensing material. The threshold impedance change value is calculated to establish a selectivity of the sensing material for the target analyte in the exposed state of the sensing material. The threshold impedance change value is modifiable to tune the selectivity of the sensing material in the frequency domain for a respective target analyte. The threshold impedance change value tunes the sensitivity of the sensing material in the frequency domain for a concentration range of the respective target analyte. The changes in respective impedance values of the sensing material across the frequency spectrum correspond to identified frequencies, and differences among the identified frequencies further indicate the concentration range of the respective target analyte. The series of inputs spans a frequency spectrum that extends beyond baseline frequencies at which ambient environmental conditions other than the target analyte dominate a set of impedance characteristics of the sensing material. In certain embodiments, the sensing material is hydrophobic. In other embodiments, the sensing material is nonpolar.

Along these lines, the sensing material includes a composition for which an impedance response in the presence of respective environmental agents is sufficiently constant that resulting impedance changes in the sensing material due to the respective environmental agents do not impact respective impedance changes due to the concentration of the target analyte. Dopants may be added to the sensing material to adjust the baseline composition and a baseline impedance profile of the sensor material. In use, the target analyte may be a chemical warfare agent selected from the group consisting of G class agents, V class agents, blistering agents, organophosphates, or combinations thereof. The target analyte may be a narcotic or opioid, such as fentanyl, carfentanil, remifentanil, or byproduct thereof. The sensor material comes in contact with the toxic chemical via solid, liquid, aerosol, vapor exposure. The sensor material can selectively respond to the toxic chemical. The sensor material can respond differently to relative humidity from the toxic chemical. The sensor material further comprises a polymer. The sensor material comprises a polymer by 1 to 90 weight percent. In other embodiments, the polymer may include poly(methyl methacrylate), polyvinylidene, fluoride, polystyrene, styrene ethylene butylene styrene, block copolymers, or combinations thereof.

To implement sensor described herein, a computerized system of sensing a target analyte in an environment may incorporate a computer having a processor and computerized memory storing software that controls a sensing circuits having an AC energy source and at least one sensing output terminal. A sensing material is connected to the AC energy source and further connected to a respective sensing output terminal of the sensing circuit, wherein the AC energy source directs a plurality of alternating inputs at respective frequencies across the sensing material. This induces a series of outputs at the respective frequencies from the sensing output terminal. An impedance detection circuit receives the series of outputs, assigning a corresponding series of impedance values to the sensing material at the respective frequencies, and transmitting the impedance values and the respective frequencies to the computer. A computerized software module is stored in the memory that identifies a change in the series of impedance values that is greater than a predetermined threshold value and indicates a presence of the target analyte at the sensing material. A transceiver is incorporated into the circuit for communications across a network. The transceiver may include a wireless transceiver, blue-tooth transceiver, and/or radio frequency transceiver. The system is configured to transmit and receive data using the transceiver.

The AC energy source may be either an AC voltage source or an AC current source, and the outputs are either an AC voltage output or an AC current output. A computerized system according to this specification, may further include a set of predetermined threshold values stored in the memory for comparing the relative change in the series of impedance values at corresponding frequency values to indicate a respective presence for a plurality of target analytes. The predetermined threshold values and the corresponding frequency values tune the system to a particular selectivity for respective target analytes. The AC energy source scans across a frequency spectrum of alternating energy inputs and induces corresponding AC outputs at the sensing output terminal for each of the alternating energy inputs. An alternating energy input such as an AC voltage source that scans across a frequency spectrum of alternating voltage inputs directs a frequency specific signal across the sensing material. The sensing material is a composition having a consistent impedance response across the frequency spectrum for environmental agents other than the target analyte. In one non-limiting embodiment, the alternating energy input is an AC current source that scans across a frequency spectrum of alternating current inputs, and the sensing material includes a composition having a consistent impedance response across the frequency spectrum for environmental agents other than the target analyte.

In a method of implementing this disclosure, sensing a target analyte in an environment includes the steps of:
(i) selecting a sensing material having a consistent impedance response in an exposed state in the presence of environmental agents other than a target analyte;
(ii) applying an alternating energy input to the sensing material and inducing an alternating energy output from the sensing material;
(iii) tracking an impedance response of the sensing material across a frequency spectrum of the alternating energy inputs;
(iv) isolating frequency induced impedance changes across the sensing material from the consistent impedance response due to the environmental agents;
(v) identifying a magnitude of the frequency induced impedance changes across the frequency spectrum, and
(vi) for impedance changes greater than a predetermined threshold across a subset of frequencies in the frequency spectrum, determining the presence of the target analyte at the sensing material.

In embodiments implementing the above noted method, the steps may further include, without limitation, doping the sensing material to offset the frequencies at which the impedance response changes in an amount greater than the predetermined threshold in comparison to an undoped sensing material, and, furthermore, tracking the frequency offset at which a plurality of changes greater than the threshold value occur within the frequency spectrum and calculating a concentration of the target analyte for each frequency offset.

In one sense and without limiting this disclosure, a system of sensing a target analyte in an environment includes a sensing material connected to a power source and further connected to a respective sensing output terminal of a sensing circuit, wherein the power source directs a plurality of alternating inputs at respective frequencies across the sensing material and induces a series of outputs at the respective frequencies from the sensing output terminal. An impedance detection circuit receives the series of outputs, assigning a corresponding series of impedance values to the sensing material at the respective frequencies, and transmitting the impedance values and the respective frequencies to the computer; and identifying a change in the series of impedance values that is greater than a predetermined threshold value and indicates a presence of the target analyte at the sensing material.

Publications cited herein are hereby specifically by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

The present disclosure has been described with reference to example embodiments, however persons skilled in the art will recognize that changes may be made in form and detail without departing from the spirit and scope of the disclosed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the exemplary embodiments is manifestly intended to be as broad as possible. For example, unless specifically otherwise noted, the exemplary embodiments reciting a single particular element also encompass a plurality of such particular elements.

Exemplary embodiments may include program products comprising computer or machine-readable media for carrying or having machine-executable instructions or data structures stored thereon. For example, the sensing electrode may be computer driven. Exemplary embodiments illustrated in the methods of the figures may be controlled by program products comprising computer or machine-readable media for carrying or having machine-executable instructions or data structures stored thereon. Such computer or machine-readable media can be any available media which can be accessed by a general purpose or special purpose computer or other machine with a processor. By way of example, such computer or machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of computer or machine-readable media. Computer or machine-executable instructions comprise, for example, instructions and data which cause a general purpose computer, special purpose computer, or special purpose processing machines to perform a certain function or group of functions. Software implementations of the present disclosure could be accomplished with standard programming techniques with rule based logic and other logic to accomplish the various connection steps, processing steps, comparison steps and decision steps.

It is also important to note that the construction and arrangement of the elements of the system as shown in the preferred and other exemplary embodiments is illustrative only. Although only a certain number of embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the assemblies may be reversed or otherwise varied, the length or width of the structures and/or members or connectors or other elements of the system may be varied, the nature or number of adjustment or attachment positions provided between the elements may be varied. It should be noted that the elements and/or assemblies of the system may be constructed from any of a wide variety of materials that provide sufficient strength or durability. Accordingly, all such modifications are intended to be included within the scope of the present disclosure. The order or sequence of any process or method steps may be varied or re-sequenced according to alternative embodiments. Other substitutions, modifications, changes and omissions may be made in the design, operating conditions and arrangement of the preferred and other exemplary embodiments without departing from the spirit of the present subject matter.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described herein with reference to block diagrams and flowchart illustrations of methods, systems, apparatuses and computer program products. It will be understood that each block of the block diagram and flowchart illustration can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagram and flowchart illustration support combinations of means for performing the specified functions, combinations of steps for performing the specified functions and program instruction means for performing the specified functions. It will also be understood that each block of the block diagram and flowchart illustration, and combinations of blocks in the block diagram and flowchart illustration, can be implemented by special purpose hardware-based computer systems that perform the specified functions or steps, or combinations of special purpose hardware and computer instructions.

The figures present an overview of an embodiment of a computer readable medium for use with the methods disclosed herein. Results can be delivered to a gateway (remote computer via the Internet or satellite) for in graphical user interface format. The described system can be used with an algorithm, such as those disclosed herein.

As may be understood from the figures, in this implementation, the computer may include a processing unit that communicates with other elements. Also included in the computer readable medium may be an output device and an input device for receiving and displaying data. This display device/input device may be, for example, a keyboard or pointing device that is used in combination with a monitor. The computer system may further include at least one storage device, such as a hard disk drive, a floppy disk drive, a CD Rom drive, SD disk, optical disk drive, or the like for storing information on various computer-readable media, such as a hard disk, a removable magnetic disk, or a CD-ROM disk. As will be appreciated by one of ordinary skill in the art, each of these storage devices may be connected to the system bus by an appropriate interface. The storage devices and their associated computer-readable media may provide nonvolatile storage. It is important to note that the computer described above could be replaced by any other type of computer in the art. Such media include, for example, magnetic cassettes, flash memory cards and digital video disks.

Further comprising an embodiment of the system can be a network interface controller. One skilled in the art will appreciate that the systems and methods disclosed herein can be implemented via a gateway that comprises a general-purpose computing device in the form of a computing device or computer.

One or more of several possible types of bus structures can be used as well, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus, and all buses specified in this description can also be implemented over a wired or wireless network connection and each of the subsystems, including the processor, a mass storage device, an operating system, network interface controller, Input/Output Interface, and a display device, can be contained within one or more remote computing devices at physically separate locations, connected through buses of this form, in effect implementing a fully distributed system.

The computer typically comprises a variety of computer readable media. Exemplary readable media can be any available media that is accessible by the computer and comprises, for example and not meant to be limiting, both volatile and non-volatile media, removable and non-removable media. The system memory comprises computer readable media in the form of volatile memory, such as random access memory (RAM), and/or non-volatile memory, such as read only memory (ROM).

In another aspect, the computer can also comprise other removable/non-removable, volatile/non-volatile computer storage media. For example and not meant to be limiting, a mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device, including by way of example, an operating system and computational software. Each of the operating system and computational software (or some combination thereof) can comprise elements of the programming and the computational software. Data can also be stored on the mass storage device. Data can also be stored in any of one or more databases known in the art. Examples of such databases comprise, DB2™, MICROSOFT™ ACCESS, MICROSOFT™ SQL Server, ORACLE™, mySQL, PostgreSQL, and the like. The databases can be centralized or distributed across multiple systems.

In another aspect, the user can enter commands and information into the computer 102 via an input device. Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit via a human machine interface that is coupled to the network interface controller, but can be connected by other interface and bus structures, such as a parallel port, game port, an IEEE 1394 Port (also known as a Firewire port), a serial port, or a universal serial bus (USB).

In yet another aspect, a display device can also be connected to the system bus via an interface, such as a display adapter. It is contemplated that the computer can have more than one display adapter and the computer can have more than one display device. For example, a display device can be a monitor, an LCD (Liquid Crystal Display), or a projector. In addition to the display device, other output peripheral devices can comprise components such as speakers and a printer which can be connected to the computer via Input/Output Interface. Any step and/or result of the methods can be output in any form to an output device. Such output can be any form of visual representation, including, but not limited to, textual, graphical, animation, audio, tactile, and the like.

The computer can operate in a networked environment. By way of example, a remote computing device can be a personal computer, portable computer, a server, a router, a network computer, a peer device, sensor node, or other common network node, and so on. Logical connections between the computer and a remote computing device can be made via a local area network (LAN), a general wide area network (WAN), or any other form of a network. Such network connections can be through a network adapter. A network adapter can be implemented in both wired and wireless environments. Such networking environments are conventional and commonplace in offices, enterprise-wide computer networks, intranets, and other networks such as the Internet.

Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems described herein can employ Artificial Intelligence techniques such as machine learning and iterative learning. Examples of such techniques include, but are not limited to, expert systems, case-based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

REFERENCES

[1] Holly Hedegaard, Margaret Warner, and Arialdi M Miniño, (US Department of Health and Human Services, Centers for Disease Control and Prevention, National Center for Health Statistics, 2017).

[2] Matthew P Prekupec, Peter A Mansky, and Michael H Baumann,"Misuse of novel synthetic opioids: a deadly new trend" Journal of addiction medicine 11 (4), 256 (2017).

[3] Joji Suzuki and Saria El-Haddad,"A review: fentanyl and non-pharmaceutical fentanyls" Drug and alcohol dependence 171, 107 (2017).

[4] R Matthew Gladden,"Fentanyl law enforcement submissions and increases in synthetic opioid-involved overdose deaths-27 states, 2013-2014" MMWR. Morbidity and mortality weekly report 65 (2016).

[5] Laura M Matz and Herbert H Hill,"Evaluation of opiate separation by high-resolution electrospray ionization-ion mobility spectrometry/mass spectrometry" Analytical chemistry 73 (8), 1664 (2001).

[6] Ahmed Jehanli, Sean Brannan, Lesley Moore, and Vina R Spiehler,"Blind trials of an onsite saliva drug test for marijuana and opiates" Journal of Forensic Science 46 (5), 1214 (2001).

[7] John F Casale, Jennifer R Mallette, and Elizabeth M Guest,"Analysis of illicit carfentanil: emergence of the death dragon" Forensic chemistry 3, 74 (2017).

[8] Simona Pichini, Renata Solimini, Paolo Berretta, Roberta Pacifici, and Francesco Paolo Busardo,"Acute intoxications and fatalities from illicit fentanyl and analogues: an update" Therapeutic drug monitoring 40 (1), 38 (2018).

[9] Coleman Harris, Jennifer Soliz, Andrew Klevitch, Michael J Bartz, Joe Rossin, Augustus W Fountain, Adam Hauser, and Gregory W Peterson,"Sensing of NO 2 with Zirconium Hydroxide via Frequency-Dependent Electrical Impedance Spectroscopy" Dalton Transactions (2017).

[10] Jennifer R. Soliz, Andrew D. Klevitch, Coleman R. Harris, Joseph A. Rossin, Amy Ng, Rhonda M. Stroud, Adam J. Hauser, and Gregory W. Peterson,"Structural Impact on Dielectric Properties of Zirconia" The Journal of Physical Chemistry C 120 (47), 26834 (2016).

[11] Gregory W Peterson, Monica Mcentee, Coleman R Harris, Andrew D Klevitch, Augustus W Fountain, J R Soliz, A Balboa, and A J Hauser,"Detection of an explosive simulant via electrical impedance spectroscopy utilizing the UiO-66-NH 2 metal-organic framework" Dalton Transactions 45 (43), 17113 (2016).

[12] Samir D Roy and Gordon L Flynn,"Solubility and related physicochemical properties of narcotic analgesics" Pharmaceutical research 5 (9), 580 (1988).

[13] Robert S Bowman, Grace M Haggerty, Roger G Huddleston, Daphne Neel, and Matthew M Flynn, (ACS Publications, 1995).

[14] Patryk Oleszczuk, Bo Pan, and Baoshan Xing,"Adsorption and desorption of oxytetracycline and carbamazepine by multiwalled carbon nanotubes" Environmental science & technology 43 (24), 9167 (2009).

[15] Roland J M Pellenq, Bernard Tavitian, Didier Espinat, and Alain H Fuchs,"Grand canonical Monte Carlo simulations of adsorption of polar and nonpolar molecules in NaY zeolite" Langmuir 12 (20), 4768 (1996).

The invention claimed is:

1. An apparatus for sensing a target analyte, the apparatus comprising:

a sensing material comprising a baseline composition and a dopant that reacts with the target analyte, wherein the dopant corresponds to a selectivity of the sensing material for the target analyte, wherein the sensing material comprises a metal hydroxide or a mixed metal hydroxide, wherein the dopant is selected from the group consisting of $CoCl_2$, $CoS_2$, $Co(NO_3)_2$, $Co(NH_3)_2$, $Co(acetate)_2$, $CuS_2$, $CuCl_2$, $Cu(NO_3)_2$, $Cu(NH_3)_2$, $Cu(acetate)_2$, $Ni(NO_3)_2$, $Ni(NH_3)_2$, $NiS_2$, $NiCl_2$, $FeCl_3$, $FeS_3$, $Fe(NO_3)_3$, $Fe(NH_3)_3$, $Ln(NO_3)x$ (Ln=lanthanides), $Ln(acetate)x$, and combinations thereof;

wherein the sensing material is in electrical communication with an energy source that directs an input of either an AC voltage or an AC current across the sensing material at a first frequency, at least a portion of the sensing material positioned in an exposed state relative to an environment;

wherein the sensing material is configured to be placed within the environment such that the exposed state comprises a concentration of the target analyte proximate the sensing material, and wherein the sensing material comprises structural features allowing a target analyte to change a composition of the sensing material by reacting with the dopant;

an impedance detection device connected to a sensing circuit and receiving an output from the sensing material, the output exhibiting a respective impedance value of the sensing material corresponding to the input for the first frequency; and wherein the respective impedance value is dependent upon the dopant, the concentration of the target analyte in the environment and the first frequency.

2. The apparatus of claim 1, wherein a respective structural feature of the sensing material is a thickness of the sensing material in which the dopant material is positioned to react with the target analyte, and wherein changes in the composition of the baseline composition are exhibited in the respective impedance value.

3. The apparatus of claim 1 wherein said dopant is present at a concentration of 1 to 90 weight percent.

4. The apparatus of claim 1, wherein said baseline composition comprises a film.

5. The apparatus of claim 1, wherein the energy source scans a series of AC voltage inputs or AC current inputs at respective frequencies in a frequency spectrum across the sensing material, and wherein the baseline composition of the sensor material comprises a baseline impedance profile, wherein a change in respective impedance values relative to the baseline impedance profile of the sensing material across the frequency spectrum is greater than a threshold impedance change value and indicates presence of the target analyte at the sensing material.

6. The apparatus of claim 5, wherein the threshold impedance change value is calculated to establish a selectivity of the sensing material for the target analyte in the exposed state of the sensing material.

7. The apparatus of claim 5, wherein the threshold impedance change value tunes the selectivity of the sensing material in the frequency domain for a concentration range of the respective target analyte.

8. The apparatus of claim 1, further comprising wherein the sensing material with the baseline composition and the dopant is hydrophobic.

9. The apparatus of claim 1, further comprising wherein the structural features of the sensing material with the baseline composition and the dopant comprise bond angles that correspond to the selectivity of the target analyte.

10. The apparatus of claim 1, further comprising wherein the sensing material with the baseline composition and the dopant comprises a dielectric constant that corresponds to the selectivity of the target analyte.

11. The apparatus of claim 10, wherein the structural features of the sensing material with the baseline composition and the dopant comprise a number of reaction sites within a thickness of the sensing material for the target analyte that determines the respective impedance value.

12. The apparatus of claim 1, wherein the dopant comprises copper sulfide and the sensing material is hydrophobic.

13. The apparatus of claim 1, wherein the sensing material with the baseline material and the dopant, comprises a dielectric constant that shifts in the presence of the target analyte.

14. The apparatus of claim 1, wherein the sensing material, with the baseline material and the dopant, is a non-polar sensing material.

15. The apparatus of claim 1, wherein the sensing material is an adsorbent material relative to the target analyte.

16. The apparatus of claim 1, wherein the sensing material comprises graphene oxide.

17. The apparatus of claim 1, wherein the sensing material is porous.

* * * * *